United States Patent
Xu et al.

(10) Patent No.: US 11,723,580 B2
(45) Date of Patent: Aug. 15, 2023

(54) OBJECTIVE EEG QUANTITATIVE MEASUREMENT METHOD FOR AMBLYOPIA

(71) Applicant: Xi'an Jiaotong University, Xi'an (CN)

(72) Inventors: Guanghua Xu, Xi'an (CN); Xiaowei Zheng, Xi'an (CN); Yunyun Wang, Xi'an (CN); Chengcheng Han, Xi'an (CN); Yongcheng Wu, Xi'an (CN)

(*) Notice: Subject to any disclaimer, the term of this patent is extended or adjusted under 35 U.S.C. 154(b) by 0 days.

(21) Appl. No.: 17/626,114

(22) PCT Filed: Dec. 27, 2019

(86) PCT No.: PCT/CN2019/128987
§ 371 (c)(1),
(2) Date: Jan. 10, 2022

(87) PCT Pub. No.: WO2021/004029
PCT Pub. Date: Jan. 14, 2021

(65) Prior Publication Data
US 2022/0287617 A1      Sep. 15, 2022

(30) Foreign Application Priority Data
Jul. 10, 2019    (CN) .......................... 201910619593.2

(51) Int. Cl.
*A61B 5/378*    (2021.01)
*G16H 50/20*    (2018.01)
(Continued)

(52) U.S. Cl.
CPC .............. *A61B 5/378* (2021.01); *A61B 5/161* (2013.01); *A61B 5/4005* (2013.01);
(Continued)

(58) Field of Classification Search
CPC ........ A61B 5/161; A61B 5/378; A61B 5/4005
See application file for complete search history.

(56) References Cited

U.S. PATENT DOCUMENTS

| 2011/0161011 A1* | 6/2011 | Hasson | ................ | A61B 5/0075 |
| | | | | 702/19 |
| 2013/0100402 A1* | 4/2013 | Ooi | .......................... | A61B 3/10 |
| | | | | 351/203 |

(Continued)

FOREIGN PATENT DOCUMENTS

CN          108803873 A       11/2018

OTHER PUBLICATIONS

Ana Rita Tuna et al., Interocular suppression, Proc. SPIE 10453, Third International Conference on Applications of Optics and Photonics, 2017, Faro, Portugal.
(Continued)

*Primary Examiner* — Devin B Henson
*Assistant Examiner* — H. Q. Nguyen
(74) *Attorney, Agent, or Firm* — Novoclaims Patent Services LLC; Mei Lin Wong

(57) ABSTRACT

The invention discloses an objective and quantitative detection method for amblyopia by electroencephalogram (EEG). The method comprises the following steps: firstly, carry out binocular dichoptic viewing display, then design a visual evoked stimulation paradigm, establish a brain-computer interface platform, build a test interaction interface, next determine an amblyopia EEG quantitative index. By using a suppression coefficient (SI) to describe the binocular suppression relationship, quantify the degree of amblyopia, and finally obtain amblyopia detection result feedback, where the computer interaction interface module presents a final amblyopia detection result to realize feedback of a user. The operation is simple and rapid, the applicability is high, and the indexes are objective and quantitative.

2 Claims, 1 Drawing Sheet

(51) Int. Cl.
*A61B 5/16* (2006.01)
*A61B 5/00* (2006.01)
*G16H 40/63* (2018.01)

(52) U.S. Cl.
CPC .......... *A61B 5/6803* (2013.01); *A61B 5/7264* (2013.01); *G16H 40/63* (2018.01); *G16H 50/20* (2018.01)

(56) References Cited

U.S. PATENT DOCUMENTS

| | | | |
|---|---|---|---|
| 2017/0035317 A1* | 2/2017 | Jung | A61B 3/0025 |
| 2017/0065168 A1* | 3/2017 | Bex | G02B 27/017 |
| 2019/0175049 A1* | 6/2019 | Welling | A61B 5/7289 |

OTHER PUBLICATIONS

Daniel H. Baker et al., Steady-State Contrast Response Functions Provide a Sensitive and Objective Index of Amblyopic Deficits, Investigative Ophthalmology and Visual Science, vol. 56, No. 2.

* cited by examiner

OBJECTIVE EEG QUANTITATIVE MEASUREMENT METHOD FOR AMBLYOPIA

CROSS REFERENCE OF RELATED APPLICATION

This is a national phase national application of an international patent application number PCT/CN2019/128987 with a filing date of Dec. 27, 2019, which claimed priority of Chinese application number 201910619593.2, filing date Jul. 10, 2019. The contents of these specifications, including any intervening amendments thereto, are incorporated herein by reference.

BACKGROUND OF THE PRESENT INVENTION

Field of Invention

The present invention relates to the technical field of brain-computer interface and central vision function examination, and particularly relates to an objective and quantitative EEG detection method for amblyopia.

BACKGROUND OF THE INVENTION

Description of Related Arts

The global incidence rate of amblyopia is as high as 3%-5%, and the main symptom is that the best vision after correction is lower than the normal value. Amblyopia is caused by defects in the development of visual center. There is abnormal competition between the two eyes, and in particular, the binocular inhibition relationship is the root cause of amblyopia. The existing subjective psychophysical amblyopia detection method is complex and diverse, and cannot detect directly from the fundamental visual center. The critical repair period of amblyopia treatment may be missed easily.

The brain-computer interface is a new type of human-computer interaction mode. Since it does not rely on human muscle tissue and peripheral nerve pathways, direct information exchange and effective interaction between the brain and the external environment can be allowed, and hence it has been widely used in medical rehabilitation and brain function testing. Wherein the steady-state visual evoked potential-based brain-computer interface is a method of inducing brain response by looking at a visual stimulus of a specific frequency, which has the advantages of strong anti-interference capability, high information transmission rate and ordinary users can be induced without training. Hence it is the most practical signal type in a common brain-computer interface. The existing subjective psychophysical amblyopia detection method has the disadvantages of having various indicators and complex methods.

SUMMARY OF THE PRESENT INVENTION

In order to overcome the problems of the conventional arts, an object of the present invention is to provide an objective and quantitative EEG measurement method for amblyopia, which is simple and quick to operate and has strong applicability and the indexes are objective and quantitative.

In order to achieve the above objective, the technical solution adopted by the present invention is as follows:

An objective and quantitative EEG measurement method for amblyopia, comprising the following steps of:

(1) Realization of dichoptic viewing: Using a 3D display and polarized glasses to realize a dichoptic viewing technology, and achieve different input information of two eyes;

(2) Visual evoked stimulation paradigm: Using the method based on steady-state motion visual evoked potential SSMVEP, induce SSMVEP by stimulating the periodic contraction and expansion of the target object, and select an optimal stimulation frequency within a motion visual sensitive frequency range in the human brain, wherein the stimulation frequency is 8 Hz and 12 Hz;

(3) Brain-computer interface platform: place the recording electrodes at the occipital area of a user's head, place the reference electrode on a position of one side of the earlobe, and place the ground electrode on the forehead of the user's head. Connect the electrodes to the input of an electroencephalogram (EEG) acquisition module. After processing amplification, filtering, and digital-analog conversion, then connect to an input of a data processing module. Next, extract characteristics of the EEG signal data by the data processing module, control the results output, and connect to the input of a computer interactive interface module;

(4) Testing of the interaction interface: the computer interactive interface presents a pattern, where, firstly, input an 8 Hz flicker paradigm for the left eye and a 12 Hz flicker paradigm for the right eye as a stimulation. After performing the stimulation for a period of time, arrange a pause for two seconds, and then perform a subsequent stimulation until a total of five stimulation is performed; a second step is: change the temporal frequency of the left eye and the right eye stimulation paradigms by using a 12 Hz flicker paradigm for the left eye and an 8 Hz flicker paradigm for the right eye, and the rest are the same;

(5) Amblyopic EEG quantitative index: Use a suppression coefficient SI to describe the binocular suppression relationship, and then quantify a degree of amblyopia:

$$SI = \frac{R_{RE} - R_{LE}}{R_{RE} + R_{LE}}$$

In the formula:
SI—Suppression coefficient between two eyes;
$R_{RE}$— Right-Eye SSMVEP response to stimulus paradigm;
$R_{LE}$— Left-Eye SSMVEP response to stimulus paradigm.

The value of the SI ranges from −1 to 1, where 0 represents a balance between the two eyes, that is, the most normal relationship between the two eyes; the closer the absolute value to 1, the stronger the suppression relationship between the two eyes and the more severe the amblyopia; a negative value indicates that the amplitude of the right eye SSMVEP is less than the amplitude of the left eye SSMVEP, that is, the left eye suppresses the right eye; a positive value indicates that the amplitude of the right eye SSMVEP is greater than the amplitude of the left eye SSMVEP, that is, the right eye suppresses the left eye;

(6) Feedback of amblyopia test result: the computer interactive interface module presents the final results of amblyopia testing and realizes feedback to users.

In step (1), the corresponding polarization display and the polarized 3D glasses are applied to realize dichoptic viewing, so that the left eye and the right eye can be presented stimulation paradigms simultaneously with different time frequencies.

The present invention further provides a corresponding objective and quantitative EEG measurement system for amblyopia, comprising:

A polarized 3D display and polarized 3D glasses to realize dichoptic viewing, so that the input information from the two eyes are different;

Recording electrodes, a reference electrode, and a ground electrode;

An EEG acquisition module, its input is connected to the different electrodes, which output EEG signal data after amplification, filtering, and digital-analog conversion processing;

A data processing module is connected to the output of the EEG acquisition module, extracting characteristics of the EEG signal data and controlling an output of the results;

A computer interactive interface module, being connected to the output of the data processing module, serving for testing the interaction interface, which is capable of presenting a visual evoked stimulation paradigm pattern and changing the presented form according to the need, and providing a final amblyopia detection result, realizing feedback to the user.

In the data processing module, the amblyopic EEG quantitative index may be preset. For example, the suppression coefficient SI is used to describe the binocular suppression relationship, thereby quantifying the degree of amblyopia.

Aiming at the defects of various indexes and complicated methods of existing subjective psychophysical amblyopia detection, the present invention provides an objective and quantitative EEG detection method for amblyopia, which is simple and rapid to operate, high in applicability, objective and quantitative in indexes, thus providing an effective method for amblyopia detection and early screening, and shows the followingadvantageous effect:

(1) Design is based on the root cause of amblyopia formation, providing an objective detection method based on EEG for amblyopia, and is convenient and fast.

(2) Providing an EEG index with the quantitative degree of amblyopia and realizing a quantitative level of amblyopia based on EEG.

(3) The selected brain-computer interface stimulation paradigm based on steady-state visual evoked potential has the advantage that the visual fatigue of the subject is not likely to be caused, the induced EEG signal is strong, and a large amount of training is not needed.

DETAILED DESCRIPTION OF THE PREFERRED EMBODIMENT

The present invention is described in detail regarding the accompanying drawing figures as follows:

An objective and quantitative EEG measurement method for amblyopia, comprising the following steps of:

(1) Realization of dichoptic viewing: Use a 3D display and polarized glasses to realize a dichoptic viewing technology, and different input information of two eyes is achieved. The 3D display can realize the 3D presentation in the left and right eye, combined with the polarized glasses, and the visual information presented to the left eye and the right eye can be different.

(2) Visual evoked stimulation paradigm: Based on steady-state motion visual evoked potential SSMVEP, by using MATLAB Psychophysics Toolbox programming to draw the periodic contraction and expansion movement of the paradigm pattern texture, SSMVEP is induced by stable stimulation. When using this method, the user is not easy to be visually fatigued. The stimulation frequency is 8 Hz and 12 Hz with a high response signal-to-noise ratio.

Figure 1:
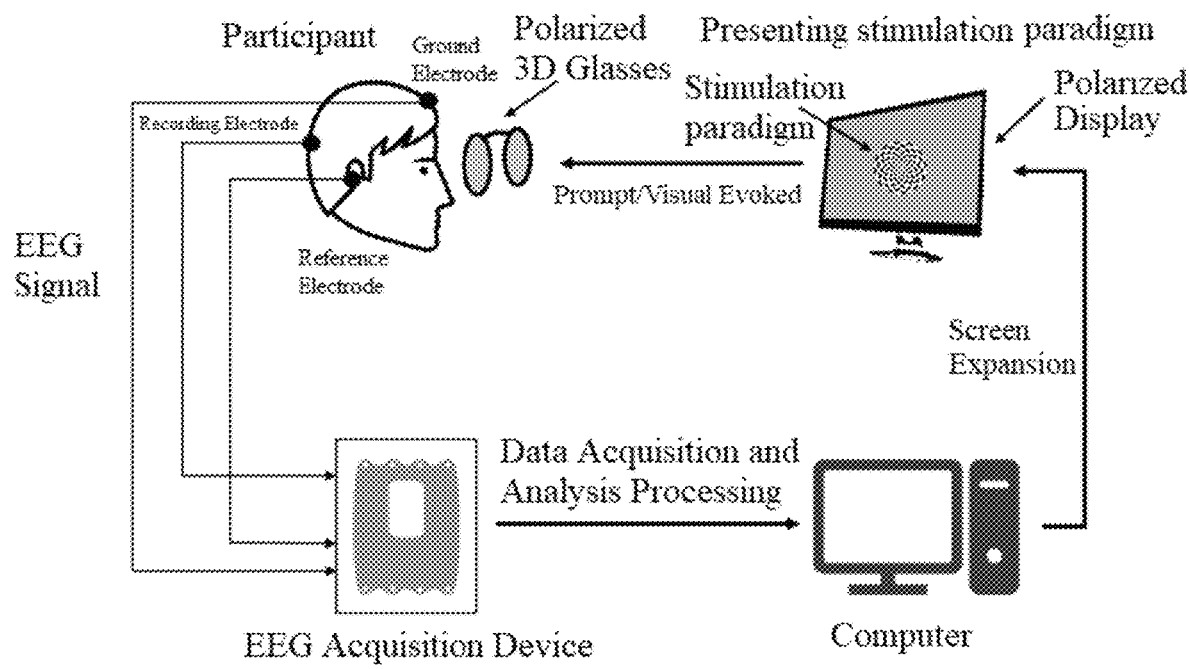
FIG. 1 is a schematic diagram of a brain-computer interface platform according to the present invention.

(3) EEG data acquisition and processing platform: Before the experiment, the electrodes are arranged according to the 10/20 system method. Place the reference electrode on the subject's left earlobe A1, the ground electrode on the subject's forehead Fpz, and six recording electrodes on the occipital area (PO3, PO4, POz, O1, O2, and Oz). Inject conductive paste into each recording electrode to ensure good contact between the electrode and the scalp. Referring to FIG. 1, the electrodes are connected to the EEG acquisition module. The EEG data is output after amplification, filtering and digital-analog conversion, and is connected to the input of the data processing module. The data processing module uses the canonical correlation analysis method to extract the features of the EEG signal data.

(4) Testing of the interaction interface: the computer interactive interface presents a pattern, firstly, inputting an 8 Hz flicker paradigm for a left eye and then a 12 Hz flicker paradigm for a right eye as a stimulation. After performing the stimulation for a period of time, arranging a pause for two seconds, and then performing a subsequent stimulation. A total of five stimulation is performed and an SSMVEP response is generated with EEG signal features are obtained by EEG acquisition and data processing. The second step: changing the temporal frequency of the left eye and the right eye stimulation paradigms, by using a 12 Hz flicker paradigm for the left eye and an 8 Hz flicker paradigm for the right eye. After stimulation for a period of time, an SSMVEP response is generated, and EEG signal features are obtained by EEG acquisition and data processing.

(5) Amblyopic EEG Quantitative Index: Use a suppression coefficient (SI) index to describe the binocular suppression relationship, and then quantify the degree of amblyopia:

$$SI = \frac{R_{RE} - R_{LE}}{R_{RE} + R_{LE}}$$

In the formula:
SI—Suppression coefficient between two eyes;
$R_{RE}$-Right-Eye SSMVEP response to stimulus paradigm;
$R_{LE}$-Left-Eye SSMVEP response to stimulus paradigm.

The value of the SI ranges from −1 to 1, where 0 represents a balance between the two eyes, that is, the normal relationship between the two eyes. The closer the absolute value to 1, the stronger the suppression relationship between the two eyes, and the amblyopia is more severe. A negative value indicates that the SSMVEP amplitude of the right eye is less than that of the left eye, that is, the left eye suppresses the right eye. A positive value indicates that the SSMVEP amplitude of the right eye is greater than that of the left eye, that is, the right eye suppresses the left eye.

(6) Feedback of test result of amblyopia: the computer interactive interface module presents the final results of amblyopia testing and realizes feedback to users.

Figure 2:
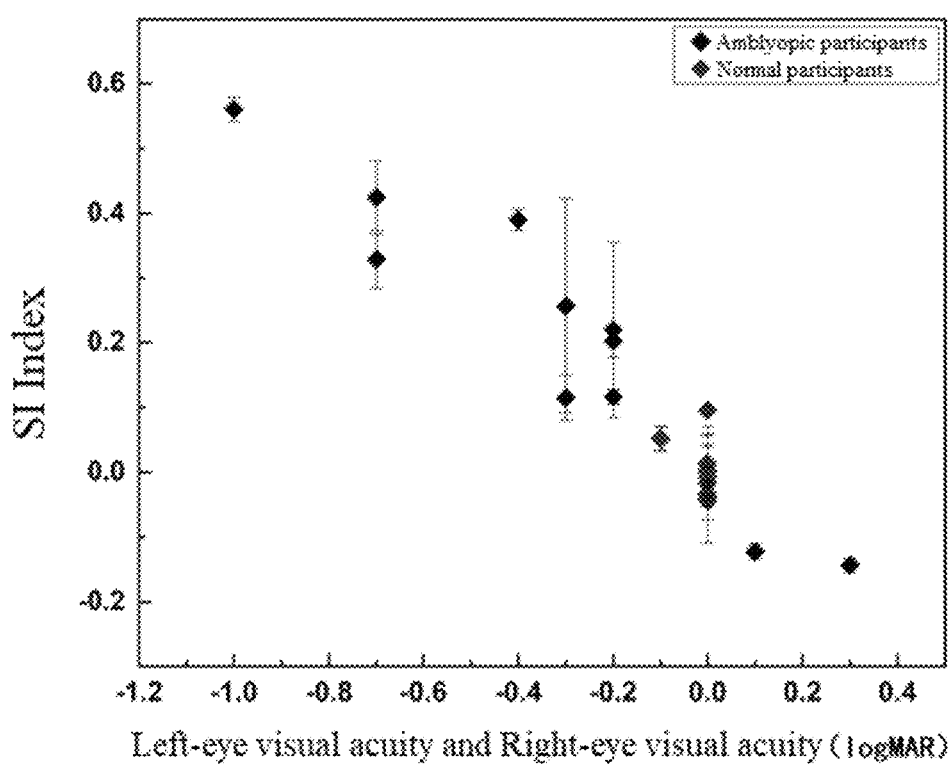
FIG. 2 is an illustration showing the correlation between interocular acuity difference and SI index.

The present invention is described in detail with reference to the embodiments of the present invention as follows:

The experiment is conducted on 11 amblyopic participants and 12 normal participants by using the method of the present invention. Place electrodes on the subjects according to the above step (3) and build a brain-computer interface platform. The user's head is 150 cm away from the computer screen. Perform experimental paradigm display and data feature extraction according to the above step (4). Obtain the SI index of each subject according to the above step (5). Give feedback of the amblyopia test results for each participant according to the above step (6). The correlation between the EEG amblyopia examination results and the subjective visual acuity difference of the left and right eyes of the subjects is shown in FIG. 2. The linear correlation coefficient r=−0.959, and the linear correlation is significant.

The present invention can base on the central optic nervous system and apply the brain-computer interface technology to realize objective and quantitative detection of amblyopia, and provide an effective means for rapid quantitative detection and early screening of amblyopia.

What is claimed is:

1. An objective and quantitative EEG measurement device to quantify a degree of amblyopia of a user, comprising:
   a dichoptic viewing module, comprising a 3D display and polarized glasses to provide the user with a dichoptic visual stimulus of different input information for each eye,
   wherein the visual stimulus is a visual evoked stimulation paradigm to induce steady-state motion visual evoked potential (SSMVEP) in the user, the stimulus having a motion visual sensitive frequency range in the human brain, wherein the stimulation frequency is 8 Hz and 12 Hz;
   an EEG acquisition module, recording electrodes configured to be placed at an occipital area PO3, PO4, POz, O1, O2 and Oz of the user's head and connected to an input of the EEG acquisition module, a reference electrode configured to be placed on an earlobe of one side of the user and connected to an input of the EEG acquisition module, and a ground electrode configured to be placed on a forehead of the user's head and connected to an input of the EEG acquisition module;
   a data processing module configured to receive output EEG signal data processed through amplification, filtering, and digital-analog conversion by the EEG acquisition module from the EEG acquisition module through an input of the data processing module, extract features of the EEG signal data by using canonical correlation analysis, and determine a degree of amblyopia of the user;
   a computer interactive interface module connected to the data processing module through an input of the computer interactive interface, wherein the computer interactive interface is configured to present an 8 Hz flicker stimulation paradigm for a left eye and a 12 Hz flicker stimulation paradigm for a right eye of the user as the visual stimulus, including a pause for two seconds after performing the stimulation for a period of time, wherein a total of five stimulations is presented to the user;
   wherein a temporal frequency of the left eye and the right eye stimulation paradigms is subsequently changed to a 12 Hz flicker stimulation paradigm for the left eye of the user and an 8 Hz flicker stimulation paradigm for the right eye of the user, and is presented a total of five times to the user with a two second pause between each stimulation;
   wherein the data processing module is configured to calculate a suppression coefficient SI to describe a binocular suppression relationship and the degree of amblyopia of the user;

$$SI = \frac{R_{RE} - R_{LE}}{R_{RE} + R_{LE}}$$

wherein in the formula:
SI represents to a suppression coefficient between the left and the right eye of the user;
$R_{RE}$ represents to the user's right eye SSMVEP response to the stimulation paradigm;
$R_{LE}$ represents to the user's left eye SSMVEP response to the stimulation paradigm;
wherein the value of the SI ranges from −1 to 1, wherein 0 represents a balance between the two eyes of the user, that is, the most normal relationship between the two eyes;
wherein the closer the value of SI is to 1, the stronger the inhibitory relationship between the two eyes of the user;
wherein a negative value of SI indicates that a SSMVEP amplitude of the right eye is less than a SSMVEP amplitude of the left eye, that is, the left eye suppresses the right eye;
wherein a positive value of SI indicates that a SSMVEP amplitude of the right eye is greater than a SSMVEP amplitude of the left eye, that is, the right eye suppresses the left eye;
wherein the computer interactive interface module is configured to output the suppression coefficient to quantify the user's amblyopia.

2. The objective and quantitative EEG measurement device to quantify a degree of amblyopia of a user according to claim 1, wherein the 3D display and polarized glasses are replaced by a polarization display and polarized 3D glasses configured to present the left eye and the right eye of the user with the stimulation paradigms simultaneously with different temporal frequencies.

* * * * *